US00PP13251P3

(12) United States Plant Patent
Utecht

(10) Patent No.: US PP13,251 P3
(45) Date of Patent: Nov. 19, 2002

(54) GERANIUM PLANT NAMED 'FISBLUDA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,119

(22) Filed: Nov. 21, 2001

(65) Prior Publication Data

US 2002/0088036 P1 Jul. 4, 2002

(51) Int. Cl.[7] ..... A01H 5/00

(52) U.S. Cl. ..... Plt./329
(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisbluda', as described and illustrated, and particularly characterized by the combined features of deep rose colored, semi-double flowers with dark red and white markings, mid season spring flowering response, medium sized inflorescences, medium green foliage with distinct zonation, and well-branched, lowly rounded, medium sized plant habit.

1 Drawing Sheet

BOTANICAL CLASSIFICATION

*Pelargonium zonale.*

VARIETY DENOMINATION

'Fisbluda'.

BACKGROUND OF THE INVENTION

The present invention comprises a new and distinct cultivar of geranium, botanically known as *Pelargonium zonale*, and hereinafter referred to by the cultivar name 'Fisbluda'.

'Fisbluda' is a product of a planned breeding program which had the objective of creating new geranium varieties with purple or magenta flower color, medium green foliage, and in combination with relatively compact plant habit.

'Fisbluda' originated from a hybridization made by the inventor Angelika Utecht in a controlled breeding program in Galdar, Gran Canaria, Spain, in 1996. The female parent was the patented cultivar 'Fisdino' (U.S. Plant Pat. No. 8,761), having red-purple flowers with red markings, large inflorescences, medium-green, zoned foliage, and fairly vigorous growth. The male parent of 'Fisbluda' was an unpatented hybrid seedling, no. K93-998-9, which was characterized by dark-pink flowers with white eyes at the bases of upper petals, larger inflorescences, medium-green, zoned foliage, and compact plant habit. (Accordingly, 'Fisbluda' is related to/is a sibling of the cultivar 'Fisdidin', U.S. Plant patent application Ser. No. 09/989,116).

'Fisbluda' was selected as one flowering plant within the progeny of the stated cross by Angelika Utecht in 1997, in a controlled environment in Galdar, Gran Canaria, Spain. The first act of asexual reproduction of 'Fisbluda' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisbluda' are firmly fixed and are retained through successive generations of asexual reproduction. The new cultivar reproduces true to type.

'Fisbluda' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisbluda' in combination distinguish this geranium as a new and distinct cultivar:

1. Carmine-rose colored flowers with deep-red and white markings;
2. Medium sized, semi-spherically shaped umbels, initially low, later well above the foliage;
3. Medium-green foliage distinct zonation;
4. Medium vigor, relatively low and wide, rounded plant habit;
5. Very well branching; and
5. Medium (mid season) spring flowering response.

Of the many commercial cultivars known to the present inventor, the most similar in comparison to 'Fisbluda' is the patented variety 'Purple Rose' (U.S. Plant Pat. No. 10,395), and 'Fisbraris' (U.S. Plant Pat. No. 9,762).

In comparison to 'Purple Rose', 'Fisbluda' has a more compact, and more uniform, round plant habit, and somewhat stronger zonation on leaves. Flowers of 'Fisbluda' are somewhat lighter in color and petals have distinct red eyes and white bases while 'Purple Rose' has weak orange-red bases but no macules.

In comparison to 'Fisbraris', 'Fisbluda' has a slightly more bluish general flower color, with macules on upper and lower petals, and with compact plant habit. Furthermore, 'Fisbluda' has medium-green foliage, in contrast to the dark-green leaves of 'Fisbraris'.

In comparison to the related cultivar 'Fisdidin', 'Fisbluda' has a more rose-red, less bluish, general hue of flower color, and upper petals display distinct white bases, which lack with 'Fisdidin'.

BRIEF DESCRIPTION OF THE DRAWING

The accompanying photographic drawing shows typical flower and foliage characteristics of 'Fisbluda' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a green-house in May 2000, in Hillscheid, Germany. The measurements were taken in Langley, British Columbia, Canada in early July, 2001, 18 weeks after planting of rooted cuttings. The plants were growing in 8 inch containers and had not been pinched.

Inflorescence:
- *Type.*—Umbel.
- *Shape.*—Semi-spherical.
- *Average diameter.*—115 mm.
- *Average depth.*—68 mm.
- *Peduncle length.*—194 mm.
- *Peduncle color.*—Light green, RHS 143 B, no anthocyanin.
- *Pedicel, length.*—31 mm.
- *Pedicel color.*—Mainly reddish, RHS 179 A, base light green RHS 144 B.
- *Number of flowers per umbel.*—About 25–30.

Corolla:
- *Average diameter.*—48.6 mm.
- *Form.*—Semi-double.
- *Shape.*—Round outline, but with a narrow gap between upper and lower petals, slightly cup-shaped.
- *Number of petals.*—Average 7.6.
- *Shape of petals.*—Obovate, base acute, upper end is rounded, margin is usually entire, near the tip (apex) very weak crenation may occur.
- *Size of petals.*—Upper petals: 26–27 mm long, 18–20 mm wide. Lower petals: 22–24 mm long, 18–20 mm wide.
- *Petaloids.*—0–1 in number; shape narrow, irregular; color RHS 57 C (Both surfaces).
- *Color (general tonality from a distance of three meters).* —Carmine-rose.
- *Color of upper petals.*—RHS 57 C.
- *Markings of upper petals.*—Medium sized, red macules: RHS 46 B, and white area (about a third of the length of the petal) at the bases, RHS 155 D, interspersed by fine red-purple veins, RHS 66 B.
- *Color of lower petals.*—RHS 57 C.
- *Markings of lower petals.*—Small red macules, RHS 57 A.
- *Color of lower surface of petals.*—Approximately RHS 66 C.
- *Color of sepals.*—Outward surface: mainly brownish, RHS 181 A to RHS 181 B, tips light green, RHS 144 A; inner surface mainly RHS 179 A, tips RHS 144 A.
- *Number of sepals.*—5.
- *Shape of sepals.*—Linear to lanceolate, acute tip, truncate base, surface with weak, very short pubescence, margin entire.
- *Size of sepals.*—10–11 mm long, 4–5 mm wide for the largest upper sepal, 2–3 mm wide with the other sepals.

Bud (just before petals unfold):
- *Shape.*—Elliptical.
- *Color (sepals).*—Light green, RHS 143 C, base brown RHS 181 A.
- *Color (petals).*—Purple-pink to rose-red, RHS 57 C.
- *Length.*—19 mm.
- *Width.*—12 mm.

Reproductive organs:
- *Androecium.*—Usually 7 fertile anthers, whitish to light pink filaments, RHS 155 D to RHS 56 A, plenty pollen, orange, RHS 30 A.
- *Gynoecium.*—One pistil, dull red style and stigma, RHS 53 B, 5 to 6 lobed stigma.
- *Fertility/seed set.*—Occasionally a few seeds are developed. Fruit: Oblong, about 6 mm in diameter, with rostrum (beak), total length about 42 mm. Seed: Oblong, 4–5 mm long, brown, RHS 177 B.

Spring flowering response period: In Hillscheid, Germany, in 2000, plants had on average 1.0 flowers opened 8 weeks after planting of rooted cuttings.

Outdoor flower production: Continuously flowering, the flower count in 2000 in Hillscheid, Germany, indicated about 2.6 inflorescences per plant in mid May.

Durability: Good stability of flower color, fair tolerance of high light intensity, relatively good rain resistance.

Lastingness of the individual flower: About 8 days at 18° C., about 18 days for the umbel.

Pest/disease resistance/susceptibility: No observations to date.

Fragrance: None.

PLANT

Foliage:
- *Shape.*—Kidney-shaped, with cordate, open base, and relatively distinct lobes for a zonal variety.
- *Margin.*—Bicrenated, somewhat wavy.
- *Texture.*—Upper surface smooth, velvety.
- *Size of leaf.*—86 mm wide, 55 mm long.
- *Color of upper surface.*—Medium green, approximately RHS 137 B to RHS 137 C.
- *Color of zonation.*—Brown, about RHS 166 A, distinctness 5 (in a range from 1 — invisible to 9 — very strong).
- *Color of lower surface.*—RHS 137 D.
- *Petioles.*—55–65 mm long, 2.5 mm in diameter, green in color, approximately RHS 137 D.

General appearance and form:
- *Stem color.*—Medium to light green, RHS 143 A.
- *Internode length.*—5–10 mm.
- *Branching pattern.*—Average 9.8 branches.
- *Size of plants.*—Height of foliage canopy 23.4 cm; width/diameter: 44.6 cm (foliage canopy was measured from the top of the soil to the foliage surface, without inflorescences).

I claim:

1. A new and distinct cultivar of geranium plant named 'Fisbluda', as described and illustrated herein.

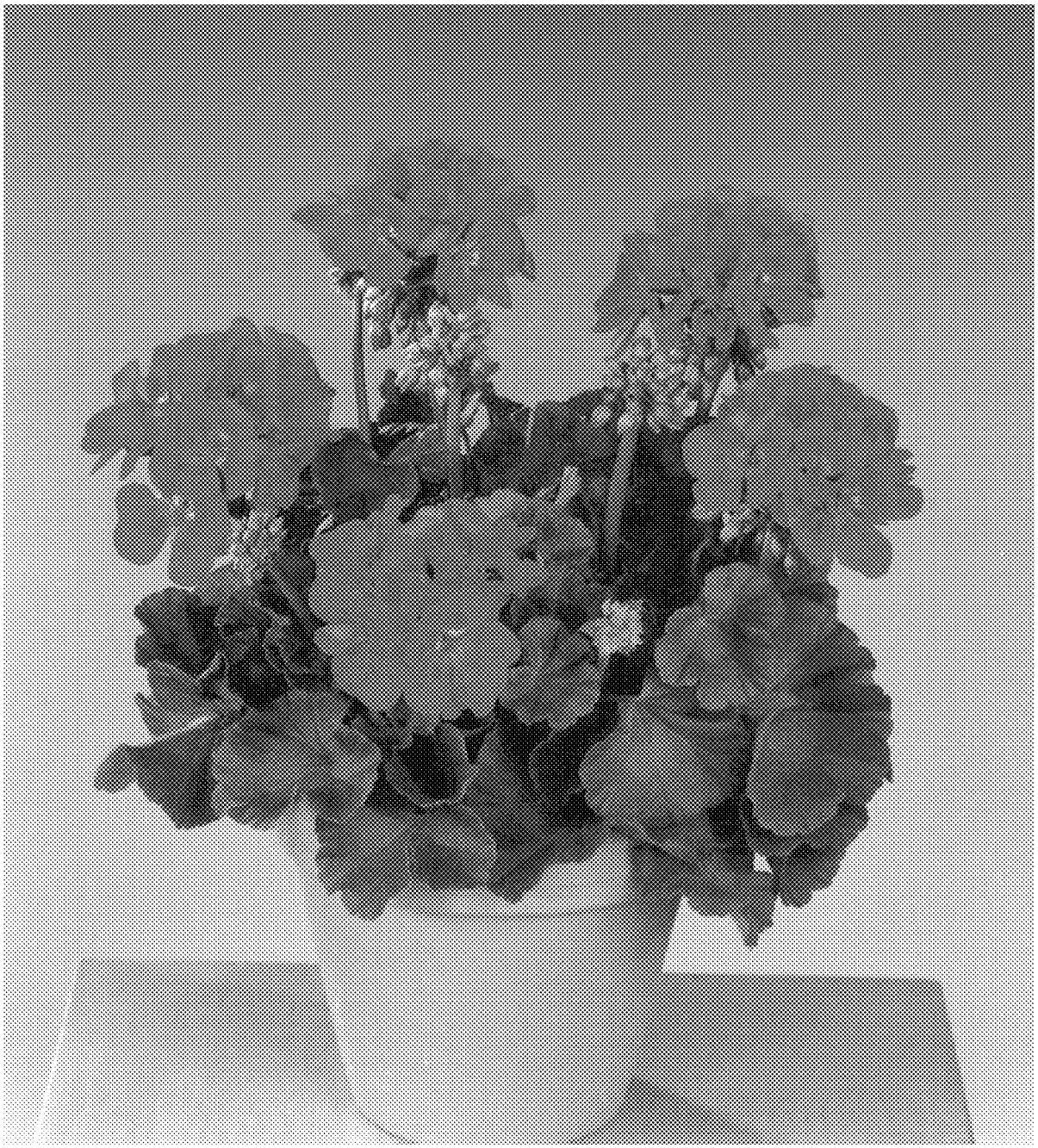

* * * * *